(12) United States Patent
Kwak

(10) Patent No.: US 8,398,563 B2
(45) Date of Patent: Mar. 19, 2013

(54) METHOD AND APPARATUS FOR HAIR CELL STIMULATION USING ACOUSTIC SIGNALS

(75) Inventor: Sangyeop Kwak, Seoul (KR)

(73) Assignee: Earlogic Korea, Inc., Seoul (KR)

( * ) Notice: Subject to any disclaimer, the term of this patent is extended or adjusted under 35 U.S.C. 154(b) by 1355 days.

(21) Appl. No.: 12/026,191

(22) Filed: Feb. 5, 2008

(65) Prior Publication Data

US 2009/0149916 A1 Jun. 11, 2009

(30) Foreign Application Priority Data

Dec. 10, 2007 (KR) ........................ 10-2007-0127477

(51) Int. Cl.
*A61B 5/00* (2006.01)
*A61N 1/00* (2006.01)
(52) U.S. Cl. .......................................... 600/559; 607/55
(58) Field of Classification Search .................. 600/559; 607/55, 56, 57
See application file for complete search history.

(56) References Cited

U.S. PATENT DOCUMENTS

| 3,531,595 A * | 9/1970 | Demaree ........................ 434/185 |
| 6,916,291 B2 * | 7/2005 | Givens et al. .................. 600/559 |
| 2005/0201574 A1 * | 9/2005 | Lenhardt ....................... 381/151 |
| 2006/0167335 A1 * | 7/2006 | Park et al. ....................... 600/25 |

* cited by examiner

*Primary Examiner* — Rene Towa
*Assistant Examiner* — Adam Eiseman
(74) *Attorney, Agent, or Firm* — Edwards Wildman Palmer LLP

(57) ABSTRACT

A method for hair cell stimulation includes determining a frequency band corresponding to damaged hair cell region in accordance with a preset algorithm, determining the frequency band corresponding to the damaged hair cell region as a target frequency band, and outputting an acoustic signal with given intensity to the target frequency band so as to stimulate the damaged hair cell region. The method treats hearing loss by acoustic signal.

15 Claims, 15 Drawing Sheets

METHOD AND APPARATUS FOR HAIR CELL STIMULATION USING ACOUSTIC SIGNALS

CROSS-REFERENCE TO RELATED APPLICATIONS

This application claims priority from Korean Patent Application No. 10-2007-127477, filed on Dec. 10, 2007, the contents of which are incorporated herein by reference in its entirety.

TECHNICAL FIELD

The present invention relates to a method and an apparatus for hair cell stimulation using acoustic signals. More particularly, it relates to a method and an apparatus for diagnosing accurately hearing ability of a user and improving the hearing ability on the basis of the diagnosed result using acoustic signals.

BACKGROUND ART

Auditory organ delivers sound to a brain. It is divided into an outer ear, a middle ear and an inner ear. Sound inputted from an outside through the outer ear vibrates a tympanic membrane, and then the sound is delivered to a cochlea of the inner ear via the middle ear.

Auditory hair cells are arranged on a basilar membrane of the cochlea. Here, the number of the hair cells arranged on the basilar membrane is approximately 12,000.

The basilar membrane has length of approximately 2.5 to 3 cm. The hair cell located on an initial part of the basilar membrane senses high frequency-sound, and the hair cell located on an end of the basilar membrane senses low frequency-sound. This is referred to as frequency specificity of the hair cell. Generally, resolution of the frequency specificity corresponding to ideal stimulation intensity equals to approximately 0.2 mm (0.5 semitone) on the basilar membrane.

Recently, since use of a portable acoustic device has been increased and people are exposed to various noises, many people have sensorineural hearing loss.

The sensorineural hearing loss is a hearing ability degeneration caused by the hair cell damage, and is generated by aging, noise exposure, drug side effect, genetic cause, etc.

Based on the severity, the sensorineural hearing loss is divided into mild hearing loss, moderate hearing loss, severe hearing loss and profound hearing loss. Generally, people who have more severe hearing loss than moderate level are hard to have a normal conversation.

Currently, it is estimated that about ten percent of total world population has the mild hearing loss in which people feel degeneration of their hearing ability. In addition, it is estimated that approximately 260,000,000 people or more have the moderate hearing loss, the severe hearing loss or the profound hearing loss in only developing countries.

In connection with this, hearing aids have been proposed. The hearing aids, however, simply amplifies external sound so that users can hear the sound; they do not prevent degeneration of the hearing ability. Moreover, the amplified sound by the hearing aids tends to degenerate hearing ability of the hearing aid users.

As a hearing teat method, pure-tone audiometry, which uses the frequency specificity of hair cells, is widely used as an international standard.

The pure-tone audiometry divides uniformly the basilar membrane into six parts through one octave interval resolution, and observes the frequency specificity of the hair cells located on each of the six parts with six frequency (for example 250, 500, 1000, 2000, 4000 and 8000 Hz) signals.

In case that normal frequency specificity is observed because the hair cell is not damaged, the frequency specificity of the hair cell may be induced in response to the signal with small sound pressure intensity. For example, in case that the frequency specificity of the hair cell corresponding to 1000 Hz is normal, electrical reaction to −1.4 dBSPL (sound pressure level) 1000 Hz pure-tone stimulus may be induced in the hair cell.

The conventional test method, however, has some problems. To diagnose hearing ability, a skilled examiner presents acoustic signals corresponding to the parts divided with only one octave resolution to a subject using a complex diagnostic device. The subject pushes a response button when s/he hears the presented signal. Because of the low frequency resolution of the conventional audiometry, it is difficult to diagnose accurately the hearing ability. Additionally, the conventional method is inconvenient to diagnose the hearing ability.

The above information disclosed in this Background Art section is only for enhancement of understanding of the background of the invention and therefore it may contain information that does not form the prior art that is already known in this country to a person of ordinary skill in the art.

SUMMARY OF THE DISCLOSURE

Accordingly, the present invention is provided to substantially obviate one or more problems due to limitations and disadvantages of the related art.

It is a feature of the present invention to provide a method and an apparatus for hair cell stimulation using acoustic signals so as to improve hearing loss.

It is another feature of the present invention to provide a method and an apparatus for hair cell stimulation using acoustic signals to diagnose more accurately hearing ability of a user.

It is still another feature of the present invention to provide a method and an apparatus for hair cell stimulation using acoustic signals to diagnose accurately hearing ability of a user at a remote place and to provide a service for improvement of hearing loss.

In one aspect, the present invention provides a method for hair cell stimulation including: (a) determining a frequency band corresponding to a damaged hair cell region; (b) determining the frequency band corresponding to the damaged hair cell region as a target frequency band; and (c) outputting an acoustic signal having a given intensity to the target frequency band so as to stimulate the damaged hair cell region.

In another aspect, the present invention provides a method for hair cell stimulation including: (a) outputting cochlear model interface comprising hair cell region images divided with 1/k octave resolution, wherein the k is a positive integer of above 2; (b) outputting an acoustic signal with a frequency band corresponding to at least one hair cell region, which is selected from the above divided hair cell region images; and (c) detecting damaged hair cell region on the basis of user's response on the outputted acoustic signal.

In still another aspect, the present invention provides a method for providing a hair cell stimulation service in a server connected electrically to a client through a network. The method includes: (a) transmitting application for diagnosis of hearing ability to the client, wherein the application outputs cochlear model interface comprising hair cell region images divided with 1/k octave resolution; (b) receiving user's response information on the acoustic signal of a frequency band corresponding to at least one of the hair cell region images; (c) on the basis of the response information, determining a frequency band corresponding to damaged hair cell region as a target frequency band; and (d) transmitting an acoustic signal of the target frequency band having given intensity to the client.

In a still further another aspect, the present invention provides a recording media readable by a computer, which performs the above methods.

In a further aspect, the present invention provides an apparatus for hair cell stimulation by acoustic signal, which includes: (a) a hearing diagnosis section configured to measure hearing threshold about a hair cell region on the basis of a user's response on a specific acoustic signal; (b) a stimulation region detecting section configured to determine a frequency band corresponding to damaged hair cell region as a target frequency band using the measured hearing threshold; and (c) a stimulation treatment section configured to output an acoustic signal with preset intensity to the determined target frequency band.

According to the present invention, a user may diagnose easily and accurately hearing ability through cochlear model interface, verify visually acoustic signal stimulation and the amount of improvement hearing ability, and improve its hearing ability.

Other aspects of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein:

FIG. 10 is a view illustrating a table in which hearing threshold measured before providing acoustic signal stimulation to a right ear is compared with that measured after the acoustic signal stimulation is provided to the right ear for ten days;

FIG. 11 is a view illustrating a table in which hearing threshold measured after acoustic signal stimulation is provided to the right ear for ten days is compared with that measured after the acoustic signal stimulation is provided to the right ear for fifteen days;

FIG. 14 is a view illustrating a table showing hearing threshold of the right ear after the acoustic signal stimulation is stopped.

DETAILED DESCRIPTION

Figure 1:
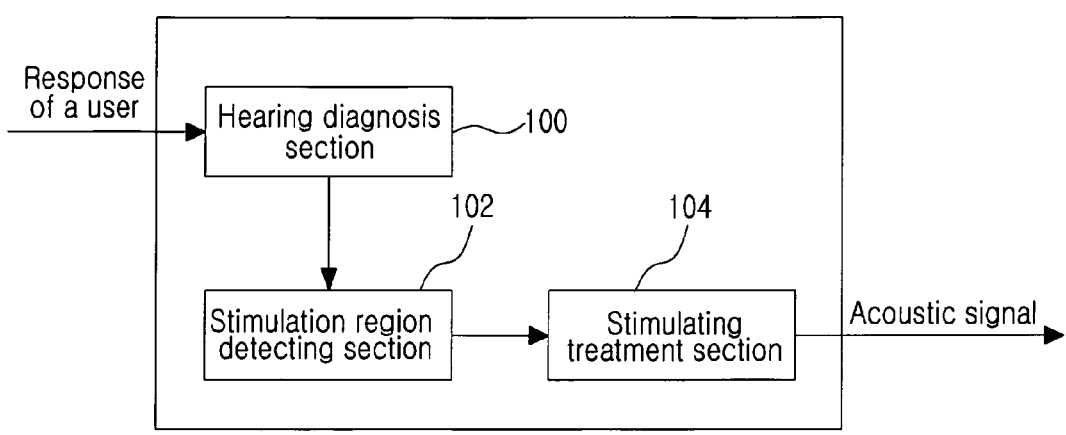
FIG. 1 is a block diagram illustrating an apparatus for hair cell stimulation according to a preferred embodiment of the present invention.

Reference will now be made in detail to the preferred embodiments of the present invention, examples of which are illustrated in the drawings attached hereinafter, wherein like reference numerals refer to like elements throughout. The embodiments are described below so as to explain the present invention by referring to the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between", "adjacent" versus "directly adjacent", etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise", "comprising,", "include" and/or "including", when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a block diagram illustrating an apparatus for hair cell stimulation according to a preferred embodiment of the present invention.

In FIG. 1, the apparatus for hair cell stimulation a includes a hearing diagnosis section 100, a stimulation region detecting section 102 and a stimulation treatment section 104.

The hearing diagnosis section 100 provides an acoustic signal corresponding to a frequency band to a user, and measures the hearing ability of a user at the frequency band through the user's response to the provided acoustic signal. Here, the hearing ability may be measured through a pure-tone audiometry (PTA), an otoacoustic emission (OAE), an evoked response audiometry (ERA), etc.

In a preferred embodiment of the present invention, unlike the conventional method with one octave frequency resolution, the hearing diagnosis section 100 provides the acoustic signal of the frequency band divided with a resolution smaller than one octave resolution to the user, and detects location of damaged hair cell(s) and the extent of the damage.

Preferably, the hearing diagnosis section 100 provides an acoustic signal of a frequency band with 1/k (is positive integer of above 2) octave resolution, more preferably 1/3 to 1/24 octave resolution to the user, and diagnoses the hearing ability of the user. In a preferred embodiment, the acoustic signal provided to the user corresponds to a medium frequency in a range of 250 Hz to 12000 Hz. In case of dividing the medium frequency range with maximum 1/24 octave resolution, whole hair cell region of the user may be divided into 134 frequency bands (134 hair cell regions).

During the hearing diagnosis, an acoustic signal of a specific frequency band selected from the 134 frequency bands is provided to the user, and the user inputs his/her response information on the provided acoustic signal of which volume is adjusted.

The user's response information on the volume adjustment is stored as a hearing threshold corresponding to the acoustic signal of the selected frequency band. Here, the hearing threshold of a frequency band means a hearing threshold of the hair cell region having frequency specificity on the selected frequency band.

The stimulation region detecting section 102 detects a stimulation region using the hearing threshold of each frequency band. Here, the detection of the stimulation region indicates detection of the hair cell region to which acoustic signal stimulation is to be provided. Particularly, the detection of the stimulation region determines the frequency band corresponding to a damaged hair cell region.

The stimulating treatment section 104 outputs the acoustic signal with a preset intensity to the frequency band of the damaged hair cell region which is determined by the stimulation region detecting section 102. Here, the acoustic signal may be provided with an intensity higher by a predetermined level than the hearing threshold of corresponding frequency band, which is pre-stored in the hearing diagnosis section 100.

In a preferred embodiment, the acoustic signal corresponds to at least one of amplitude modulated tone, frequency modulated tone, pulse tone and amplitude modulated narrowband noise, or combination of the tones and the noise.

Furthermore, in case that several hair cell regions are damaged, the acoustic signal may be provided to the damaged hair cell regions in an order of damage severity, randomly, or simultaneously.

When the acoustic signal is provided to the damaged hair cell regions of the user with various intensities, types or orders, the user's hearing ability may be improved.

Hereinafter, an apparatus for hair cell stimulation according to a preferred embodiment of the present invention will be described in detail with reference to FIG. 2.

Figure 2:
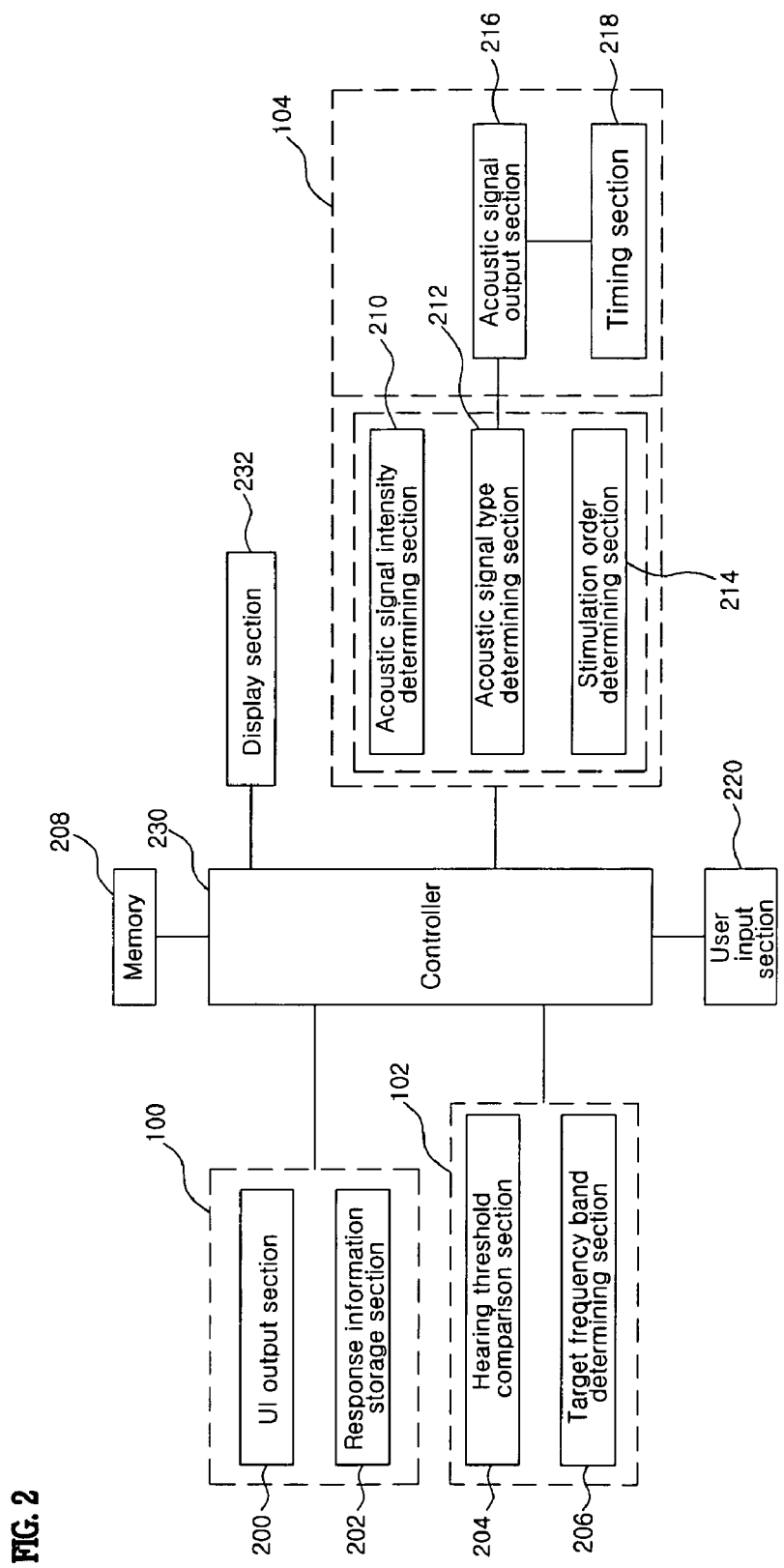
FIG. 2 is a detail block diagram illustrating an apparatus for hair cell stimulation according to a preferred embodiment of the present invention.

As shown in FIG. 2, the hearing diagnosis section 100 includes an UI output section 200 and a response information storage section 202.

Figure 3:
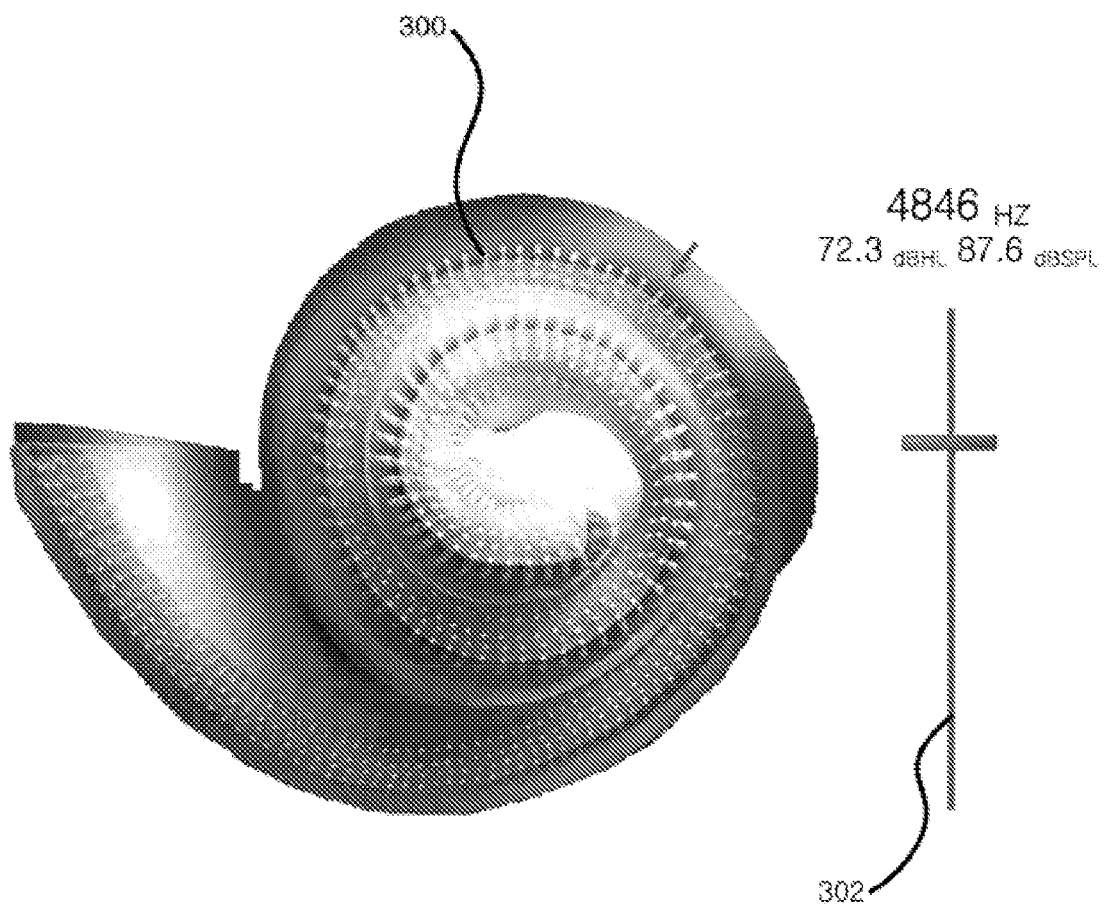
FIG. 3 is a view illustrating cochlear model interface according to a preferred embodiment of the present invention.

The UI output section 200 displays cochlear model interface shown in FIG. 3 on a display section 232 so that the subject not a skilled expert can diagnose its hearing ability by itself.

As shown in FIG. 3, the cochlear model interface has an image 300 corresponding to the hair cell regions divided with high resolution. Here, since whole frequency range for hearing diagnosis corresponds to the medium frequency, i.e. 250 Hz to 12000 Hz, the cochlear model interface may have 134 hair cell region images 300 in case of dividing the medium frequency range with 1/24 octave resolution.

In case that the user selects one of the hair cell region images 300 in order to measure the hearing ability, an acoustic signal of a frequency band matched with the selected hair cell region image is outputted. Here, the frequency band matched with the hair cell region image means the frequency band to which corresponding hair cell region has frequency specificity. In addition, the hair cell region image 300 may be selected by using a key button, a mouse, a touch screen method, etc.

In case that the acoustic signal is outputted, the user may adjust the intensity of the acoustic signal using volume control 302, and inputs response information about an intensity point at which the acoustic signal is not heard.

The response information storage section 202 receives the response information corresponding to each of the acoustic signals from a user input section 220 and stores the received response information. Here, the user input section 220 may be a keypad, a mouse or a touch screen. In a preferred embodiment, the response information may be stored as the hearing threshold of the frequency band related to corresponding acoustic signal as mentioned above.

The hearing diagnosis on several hair cell regions can be performed by the above-described method.

In FIG. 2, the stimulation region detecting section 102 includes a hearing threshold comparison section 204 and a target frequency band determining section 206.

The hearing threshold comparison section 204 compares the user's hearing threshold stored in the response information storage section 202 with a reference hearing threshold. The hearing threshold comparison section 204 determines whether or not the hearing threshold of the measured frequency band is higher than the reference hearing threshold.

Based on the comparison result, the target frequency band determining section 206 determines a frequency band which requires treatment as a target frequency band. Here, the determination of the target frequency band indicates detection of damaged hair cell region, and the target frequency band may be determined in a unit of 1/k octave resolution like in the hearing diagnosis section 100. However, the determination of the target frequency band is not limited to this. For example, a frequency band range corresponding to the adjacent hair cell regions, in which the hair cell regions have high hearing threshold region, may be determined as the target frequency band.

Information about one or more target frequency band determined and information about order of damage severity are stored in a memory 208 in accordance with user identification information.

The stimulating treatment section 104 includes an acoustic signal intensity determining section 210, an acoustic signal type determining section 212, a stimulation order determining section 214, an acoustic signal output section 216 and a timing section 218. The stimulating treatment section 104 provides the acoustic signal to the user using the information stored in the memory 208.

The acoustic signal intensity determining section 210 determines intensity of the acoustic signal to be provided to the user.

Preferably, the acoustic signal intensity determining section 210 determines one higher by 3 decibel to 20 decibel than the hearing threshold of each target frequency band as the acoustic signal intensity of the corresponding target frequency band.

In case that the target frequency band is determined as the frequency band range corresponding to the hair cell regions located continuously, the acoustic signal intensity determining section 210 may determine one higher by 3 decibel to 20 decibel than the average value of the hearing thresholds of the hair cell regions as the acoustic signal intensity.

More preferably, the acoustic signal intensity may be determined by a range of 3 decibel to 10 decibel.

Considering user's preference, hearing loss severity, and/or target frequency band, the acoustic signal type determining section 212 determines type of the acoustic signal to be provided to the user.

In a preferred embodiment, source of the acoustic signal may include amplitude modulated tone, frequency modulated tone, continuous tone, pulse tone, amplitude modulated narrowband noise, etc. Here, the acoustic signal type determining section 212 determines at least one of the tones and the noise or combination of the tones and the noise as the acoustic signal to be provided to the user.

Considering user's preference, hearing loss severity, and/or adjacency of the target frequency bands, the simulation order determining section 214 determines output order of the acoustic signals corresponding to several target frequency bands.

Preferably, the stimulation order determining section 214 may determine the output order so that the acoustic signal is outputted in sequence from the frequency band corresponding to the most damaged hair cell region. However, the above output order is not limited as the order mentioned above. For example, the acoustic signal may be randomly or simultaneously outputted to the several target frequency bands.

The acoustic signal output section 216 outputs the acoustic signal with the thus-determined intensity, type and order. Here, in case that the several target frequency bands exist and the acoustic signals of the target frequency bands are individually outputted, output time of the each acoustic signal may be set. The timing section 218 detects whether or not the output time of the each acoustic signal is finished, and controls the acoustic signal output section 216 in accordance with the detection result so that the acoustic signal output section 216 outputs an acoustic signal of next target frequency band or finishes output of the acoustic signal.

In a preferred embodiment, the UI output section 200 displays information on the cochlear model interface when the acoustic signal for hearing treatment of the user is outputted, wherein the user visually recognizes presence or absence, intensity, type, etc of the acoustic signal through the information.

For example, the UI output section 200 may change color or size of the hair cell region image 300 corresponding to the frequency band (target frequency band) of the acoustic signal outputted now in accordance with control of a controller 230.

In case that the acoustic signal is amplitude modulated tone, the UI output section 200 may change color or size of corresponding hair cell region image 300 synchronizing with amplitude change of the amplitude modulated tone.

In case that the acoustic signal is frequency modulated tone, the UI output section 200 may change color or size of the hair cell region image 300 corresponding to the changed frequency synchronizing with frequency change of the frequency modulated tone.

In case that the acoustic signal is continuous tone or pulse tone, the UI output section 200 may change color or size of corresponding hair cell region image 300 so that the user recognizes the currently provided acoustic signal as the continuous tone or pulse tone.

In a preferred embodiment, the user may verify intuitively through the cochlear model interface whether or not the hearing ability of each hair cell region is improved.

The UI output section 200 exhibits the hair cell region image 300 of the target frequency band differently from other hair cell image. Additionally, the UI output section 200 may indicate the image 300 of the damaged hair cell region with color or size varied in accordance with damage severity.

After the above stimulation through the acoustic signal (hereinafter, referred to as "acoustic signal stimulation"), the UI output section 200 changes color or size of corresponding hair cell region image 300 in accordance with the extent of improvement of each hair cell region so that the user recognizes the extent of hearing improvement.

The extent of hearing improvement may be determined by measuring again hearing threshold of the target frequency band.

Hereinafter, a method for hearing diagnosis and a method for hearing improvement will be described in detail with reference to accompanying drawings FIG. 4 and FIG. 5.

Figure 4:
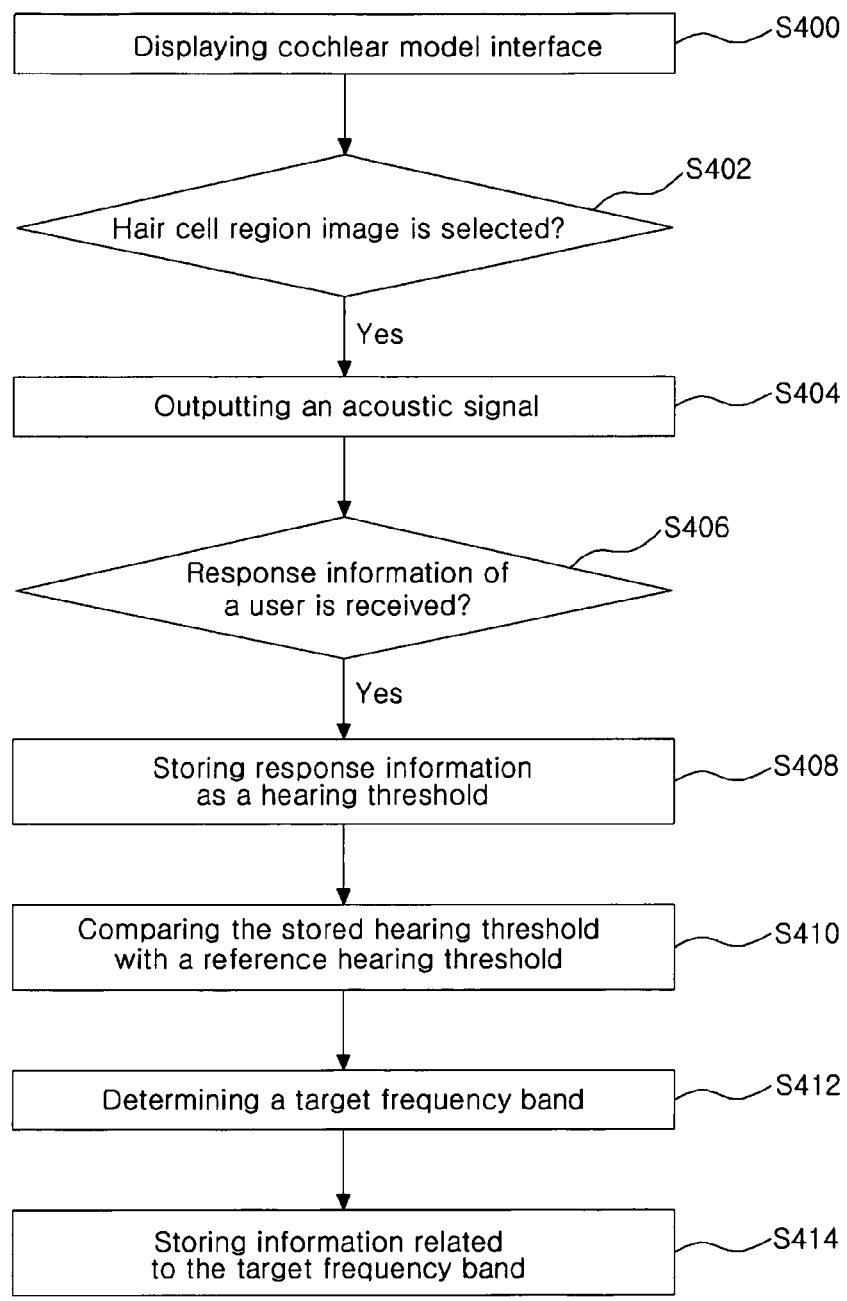
FIG. 4 is a flow chart illustrating a diagnostic process of hearing ability according to a preferred embodiment of the present invention.

FIG. 4 is a flow chart illustrating a diagnostic process of hearing ability according to a preferred embodiment of the present invention. In this example, the display section 232 of the apparatus for hair cell stimulation is embodied with a touch screen.

Referring to FIG. 4, the apparatus for hair cell stimulation displays the cochlear model interface shown in FIG. 3 on the touch screen 232 in case that the user requests diagnosis of his/her hearing ability in step 400. Here, the cochlear model interface has several hair cell region images in which frequency bands generated by dividing medium frequency with maximum 1/24 octave resolution are visualized.

In step S402, it is determined whether or not the user selects the hair cell region image 300 displayed on the cochlear model interface.

In step S404, in case that the user selects the hair cell region image 300, an acoustic signal of the frequency band corresponding to the hair cell region related to the selected image 300 is outputted.

In step S406, it is determined whether or not the user's response information on the acoustic signal is received.

The user may adjust volume in accordance with whether or not the user hears the acoustic signal, and input the response information on the intensity level at which the acoustic signal is not heard.

In step S408, the user's response information is stored as the hearing threshold of the frequency band corresponding to each of the acoustic signals.

In step S410, the user's hearing threshold is compared with the reference hearing threshold after the response information input is finished.

In step S412, the target frequency band is determined by the comparison, wherein the acoustic signal stimulation is required for the target frequency band.

In step S414, information concerning the target frequency band is stored in the memory 208. Here, the information concerning the target frequency band may include user identification information, hearing threshold information of the frequency band on which hearing diagnosis is performed, target frequency band information, order information on damage severity, etc.

In case that the acoustic signals are divided with 1/24 octave resolution, the target frequency band may be determined to the corresponding individual frequency band of each acoustic signal. However, the determination of the target frequency band is not limited to this method. That is, specific frequency band range in which the average of hearing thresholds of the frequency bands is higher than a reference value may be determined as the target frequency band. For example, in case of measuring the hearing ability using each of the acoustic signals corresponding to the frequency bands of 5920 Hz to 6093 Hz (first interval), 6093 Hz to 6272 Hz (second interval) or 6272 Hz to 6456 Hz (third interval) generated by dividing the medium frequency with 1/24 octave resolution, the target frequency band may be determined in a unit of intervals or in a new interval having the above three intervals, i.e. 5920 Hz to 6456 Hz.

Figure 5:
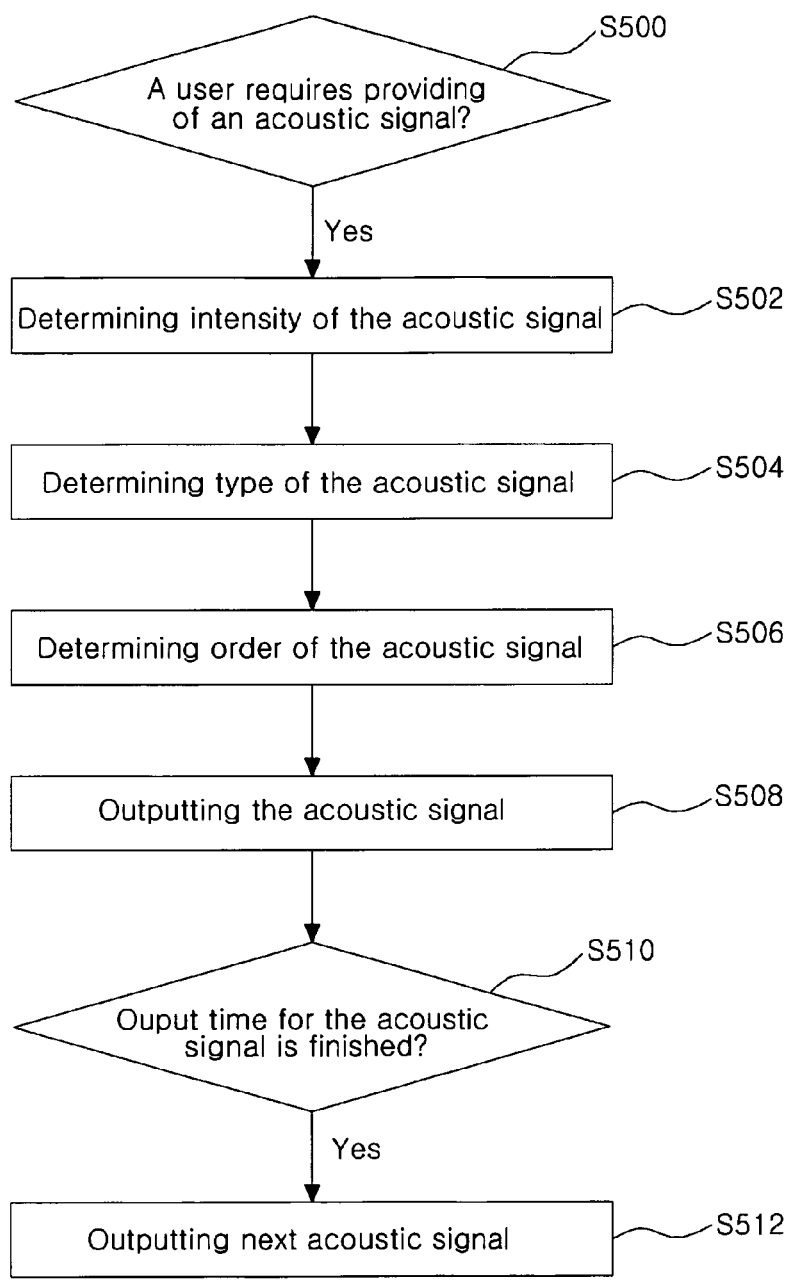
FIG. 5 is a flow chart illustrating a process of hair cell stimulation according to a preferred embodiment of the present invention.

FIG. 5 is a flow chart illustrating a process of hair cell stimulation according to a preferred embodiment of the present invention.

After the target frequency band is determined as mentioned above, the apparatus for hair cell stimulation determines intensity, type, order, etc of the target frequency band, and outputs the acoustic signal for improving the hearing ability of the user in accordance with the determination result.

Referring to FIG. 5, in case that the user requests presentation of the acoustic signal in step S500, the apparatus for hair cell stimulation reads information concerning the target frequency band from the memory 208 and then determines intensity of the acoustic signal of the target frequency band in step S502.

In steps S504 and S506, type and output order of the acoustic signal are determined.

As described above, the output order of the acoustic signal may be determined in accordance with damage severity, or determined so that the acoustic signal is randomly or simultaneously outputted.

In step S508, the acoustic signal is outputted in accordance with the determined intensity, type and order.

In step S510, in case that the acoustic signal is outputted in accordance with damage severity or is randomly outputted, it is determined whether or not output time of one acoustic signal is finished.

In step S512, in case that the output time is finished, another acoustic signal corresponding to next target frequency band is outputted.

On the other hand, in case that the acoustic signal is outputted, the apparatus for hair cell stimulation synchronizes the cochlear model interface with output, amplitude change, frequency change or pulse period of the acoustic signal, and changes color or size of the hair cell region image 300 of the cochlear model interface in accordance with the synchronization.

The method for hair cell stimulation is provided through a computer or a portable terminal established by the user or in a hospital, etc. In addition, the method may be provided through a network at a remote place.

Figure 6:
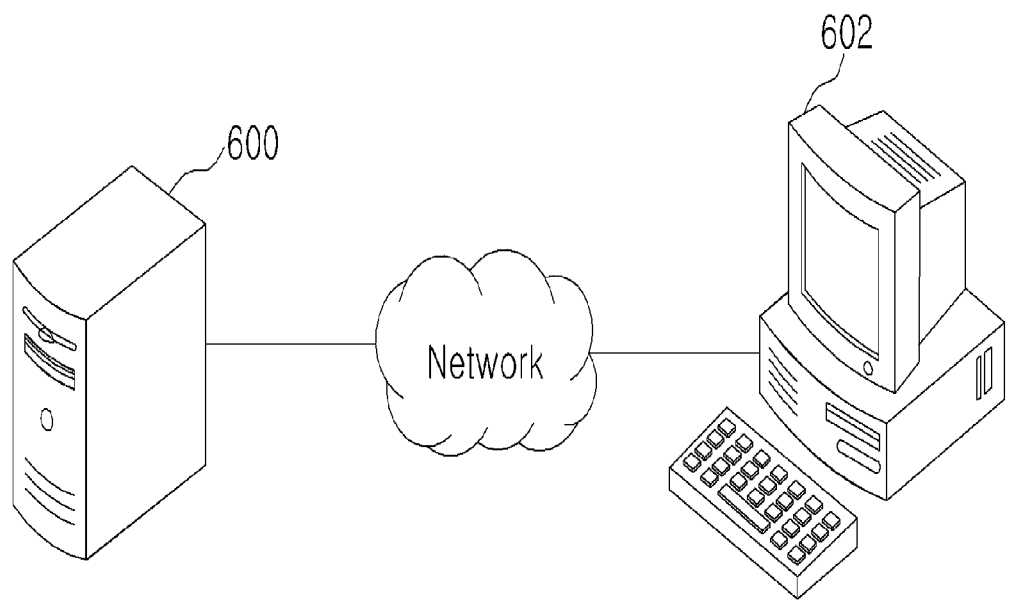
FIG. 6 is a view illustrating a hearing improvement service system according to a preferred embodiment of the present invention.

FIG. 6 is a view illustrating a hearing improvement service system according to a preferred embodiment of the present invention.

In FIG. 6, the hearing improvement service system includes a hearing improvement sever 600 connected electrically to at least one user client 602 through a network. Here, the network includes a wire network having an Internet and a private line and a wireless network having a wireless Internet, a mobile communication network and a satellite network.

The hearing improvement sever 600 provides an application for outputting the cochlear model interface shown in FIG. 3 to the user client 602 in accordance with request of the user. Here, the hearing improvement sever 600 may provide the application through various methods such as a download, webpage-inserted form, etc.

In case that the user selects a certain hair cell region image 300 through the cochlear model interface, the above application outputs an acoustic signal of a frequency band corresponding to the hair cell region selected by the user.

Subsequently, in case that the user inputs the response information about an intensity level at which the acoustic signal is not heard in accordance with volume control of the acoustic signal, the user client 602 transmits the response information to the hearing improvement sever 600.

The hearing improvement sever 600 includes the stimulation region detecting section as shown in FIG. 1 and FIG. 2, and determines the target frequency band requiring treatment on the basis of the transmitted response information of the user.

Additionally, the hearing improvement sever 600 stores information concerning the target frequency band and determines intensity, type, order, etc of the target frequency band. Upon user's request, the hearing improvement sever 600 provides the acoustic signal corresponding to the target frequency band to the user client 602 through the network in accordance with the determined result.

The user client 602 may be embodied with a terminal which operates the application and is equipped with a speaker, and include a desktop, a laptop, a mobile communication terminal, etc.

The user client 602 stimulates the hair cell of the user by outputting the acoustic signal provided from the hearing improvement sever 600.

The extent of hearing improvement by the apparatus for hair cell stimulation of the present embodiment is verified through an experiment.

Figure 7:
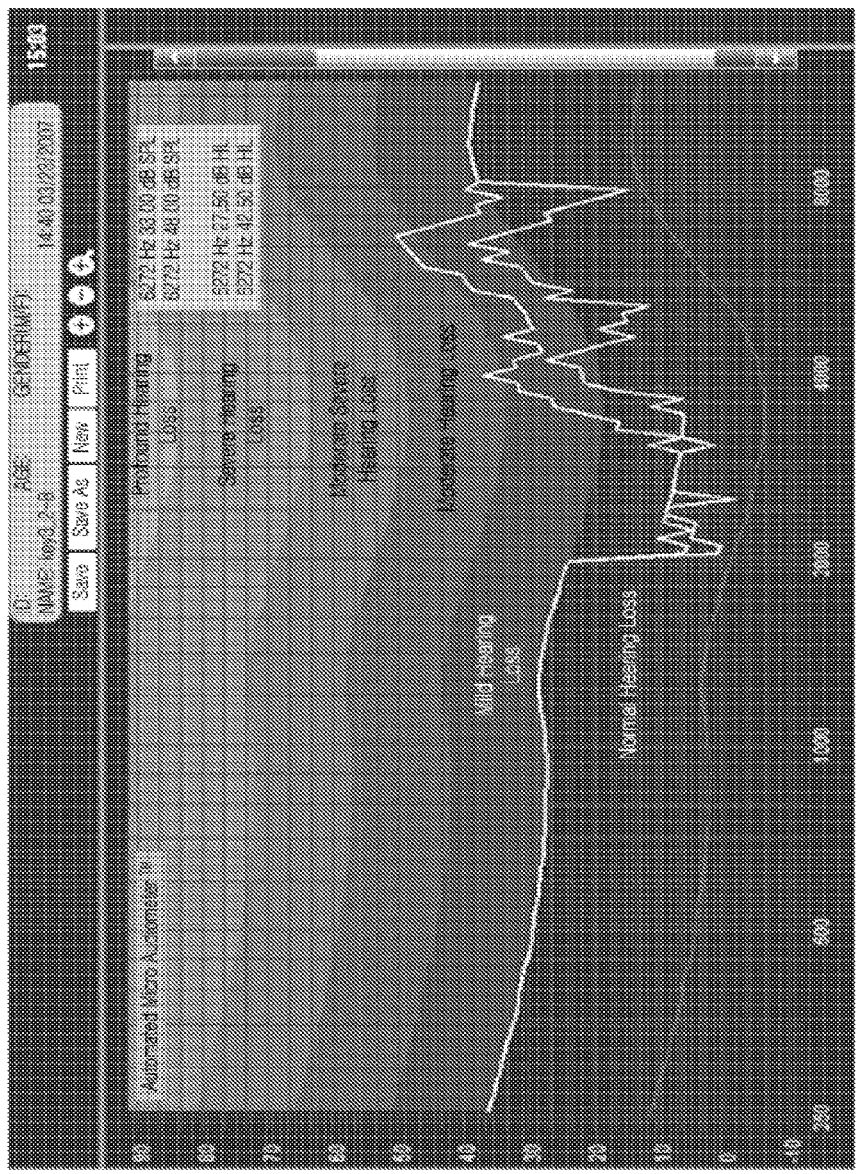
FIG. 7 is a view illustrating a graph indicating pure-tone audiometry result of a subject.

FIG. 7 is a view illustrating a graph indicating pure-tone audiometry result of a subject. Particularly, FIG. 7 shows result generated by examining hearing ability in the range of 2000 Hz to 8000 Hz with 1/24 octave resolution using the hearing diagnosis section 100.

As shown in FIG. 7, right ear of the subject has a mild to moderate hearing loss in a frequency region of 3000 Hz to 7000 Hz.

Figure 8:
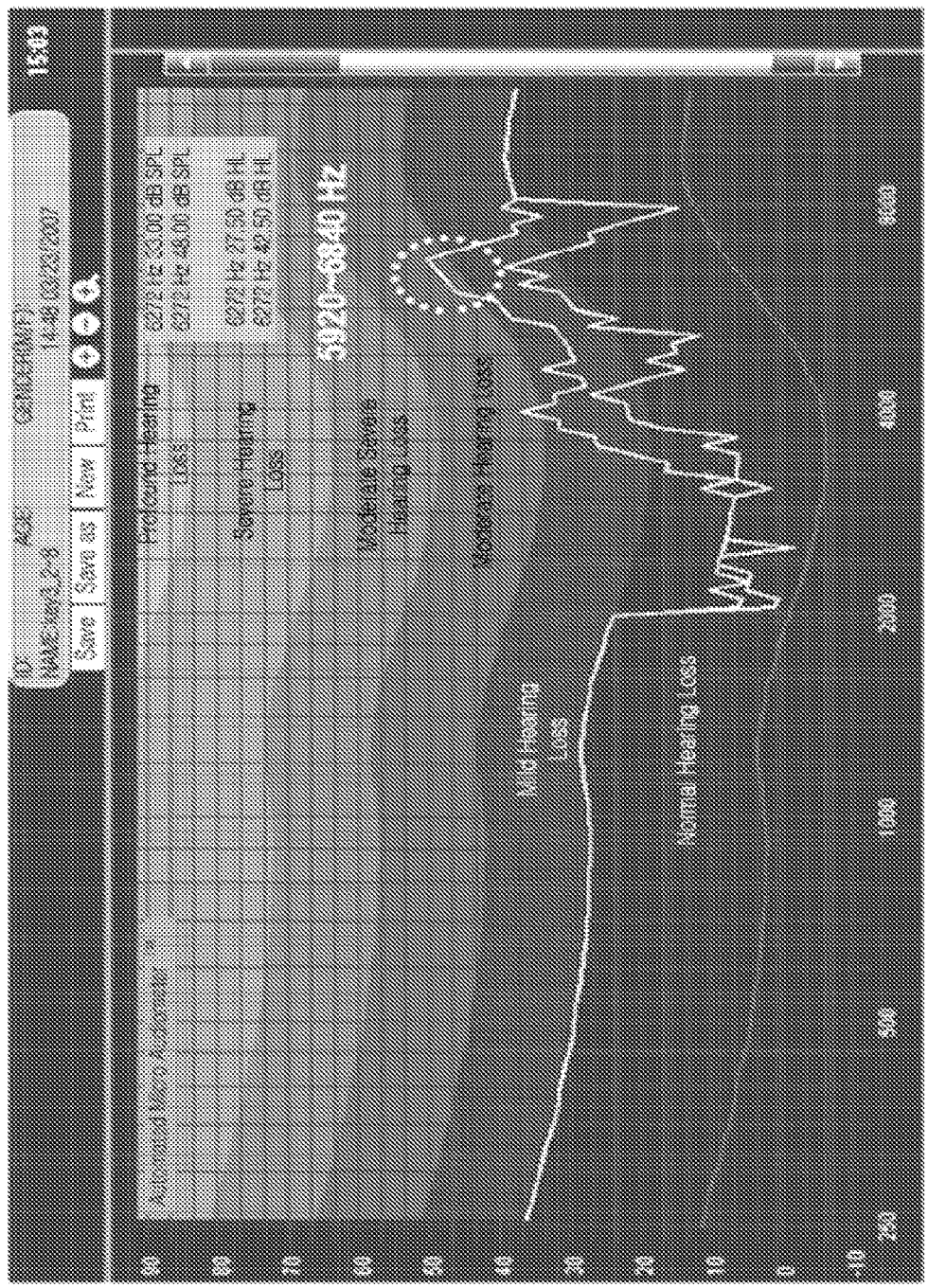
FIG. 8 is a view illustrating the target frequency band determined for the subject in FIG. 7.

FIG. 8 is a view illustrating the target frequency band determined for the subject in FIG. 7. Particularly, a frequency band range of 5920 Hz to 6840 Hz showing approximately 50 dBHL of hearing threshold is determined as the target frequency band for the subject in FIG. 7.

The acoustic signal such as frequency modulated tone or amplitude modulated narrowband noise related to the target frequency band determined in FIG. 8 is provided to the right ear for thirty minutes in the morning and evening over fifteen days. Here, the intensity of the acoustic signal is adjusted to 5 dBSL (sensational level) to 10 dBSL.

Figure 9:
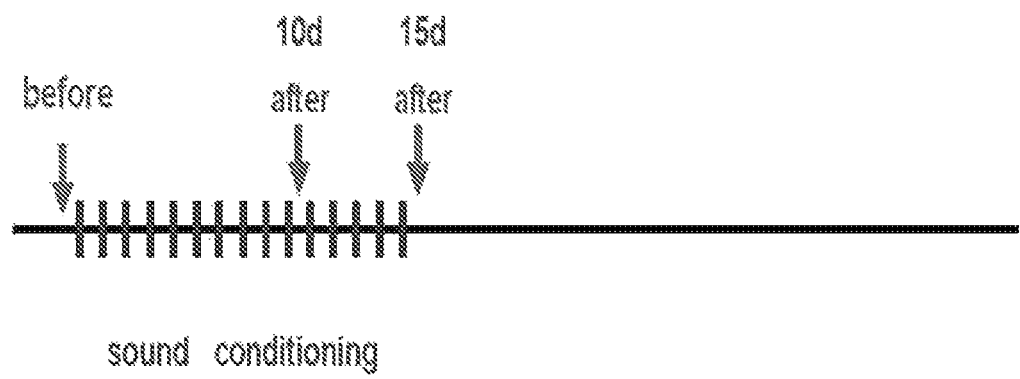
FIG. 9 is a view illustrating schedule for acoustic signal stimulation.

FIG. 9 is a view illustrating schedule for acoustic signal stimulation. Particularly, hearing ability is measured before the acoustic signal stimulation is provided (first test), after providing the acoustic signal stimulation for ten days (second test), and after providing the acoustic signal stimulation for fifteen days (third test), and then hearing thresholds corresponding to the measurement are compared.

In each test, in order to avoid misinterpretation due to experimental error, the hearing ability is measured ten times with ¹⁄₂₄ octave resolution and then average of the measured values is used as the hearing ability.

Figure 10:
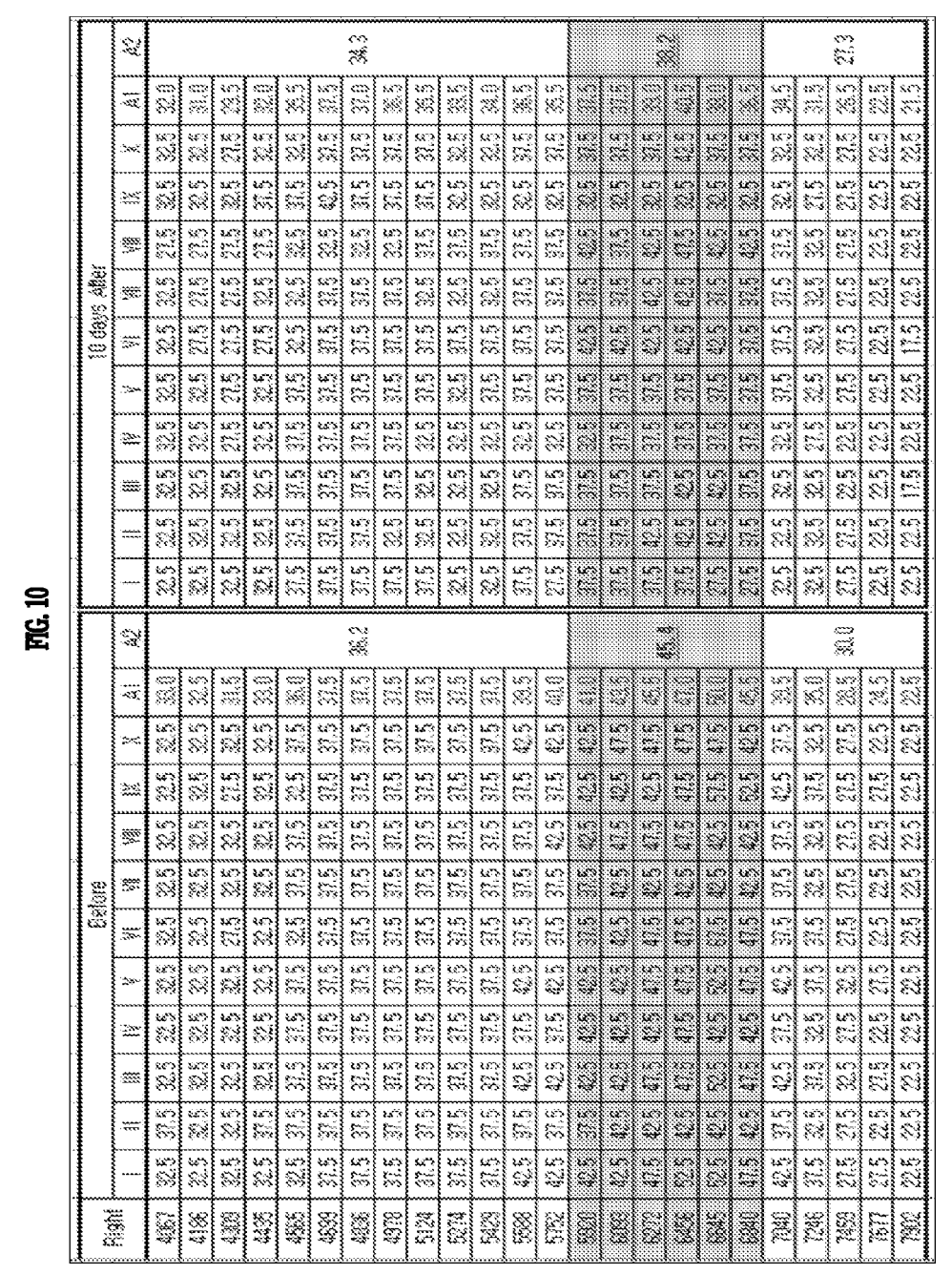
Figure 11:
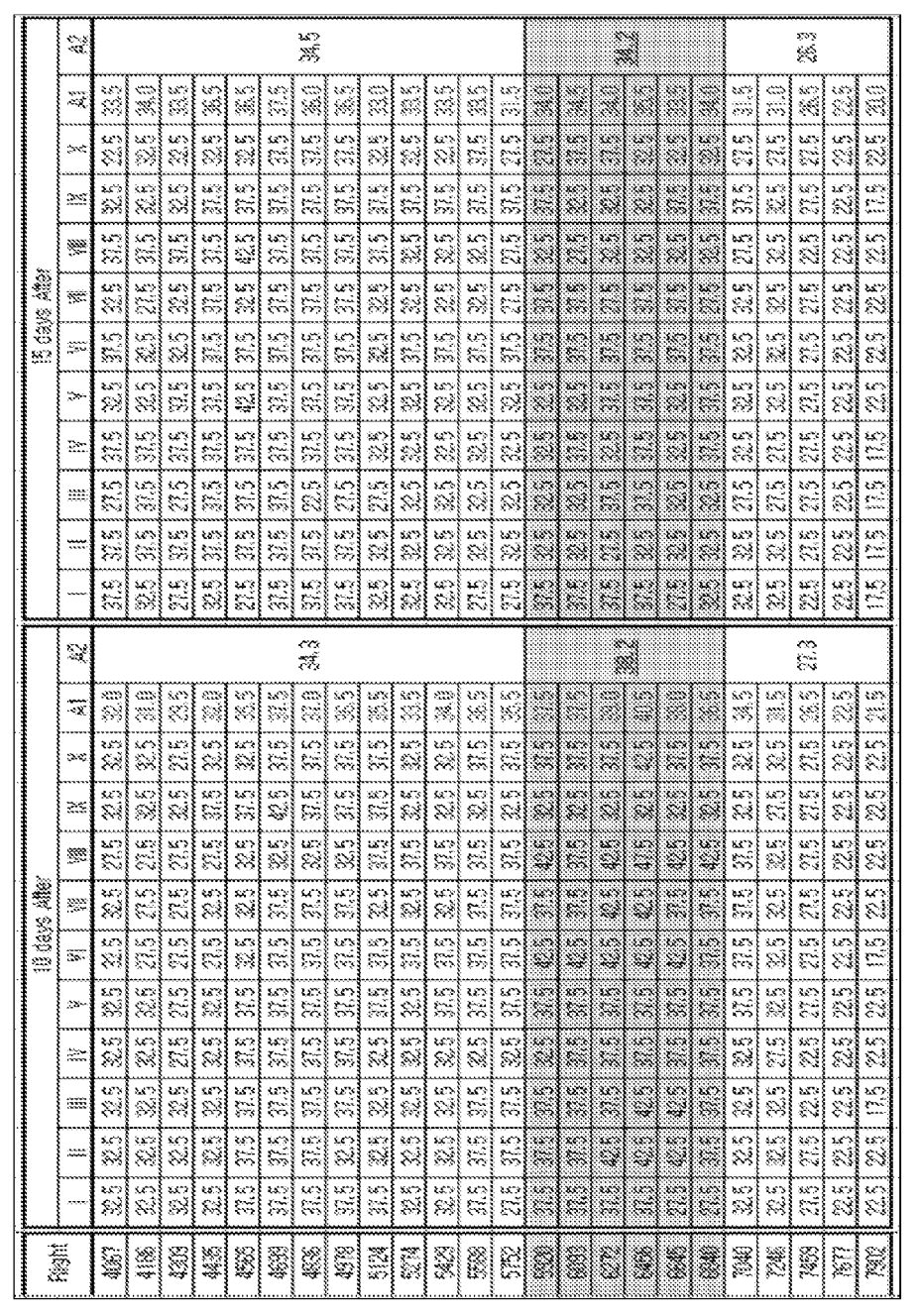

FIG. 10 is a view illustrating a table in which hearing threshold measured before providing the acoustic signal stimulation to a right ear is compared with that measured after the acoustic signal stimulation is provided to the right ear for ten days. FIG. 11 is a table in which the hearing threshold measured after acoustic signal stimulation is provided to the right ear for ten days is compared with that measured after the acoustic signal stimulation is provided to the right ear for fifteen days.

Referring to FIG. 10 and FIG. 11, the hearing threshold of the target frequency band becomes lower after the acoustic signal stimulation is provided, i.e. the hearing ability is improved.

Figure 12:
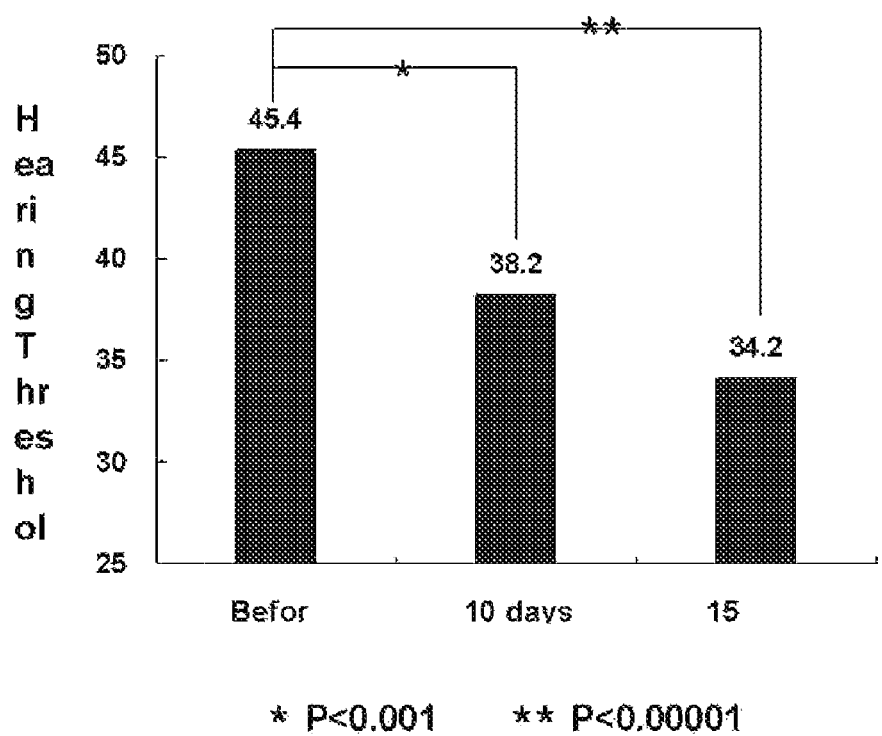
FIG. 12 is a view illustrating a graph showing hearing threshold of the right ear before and after the acoustic signal stimulation is provided.

FIG. 12 is a view illustrating a graph showing the hearing threshold of the right ear before and after the acoustic signal stimulation is provided.

In FIG. 12, before the acoustic signal stimulation is provided, hearing threshold (right ear) of a frequency band of 5920 Hz to 6840 Hz equals to 45.4 dBHL. However, after the acoustic signal stimulation is provided for ten days, the hearing threshold of the frequency band is lowered to 38.2 dBHL. In addition, the hearing threshold is more lowered to 34.2 dBHL after the acoustic signal stimulation is provided for fifteen days. The extent of the hearing threshold reduction is statistically significant.

Figure 13:
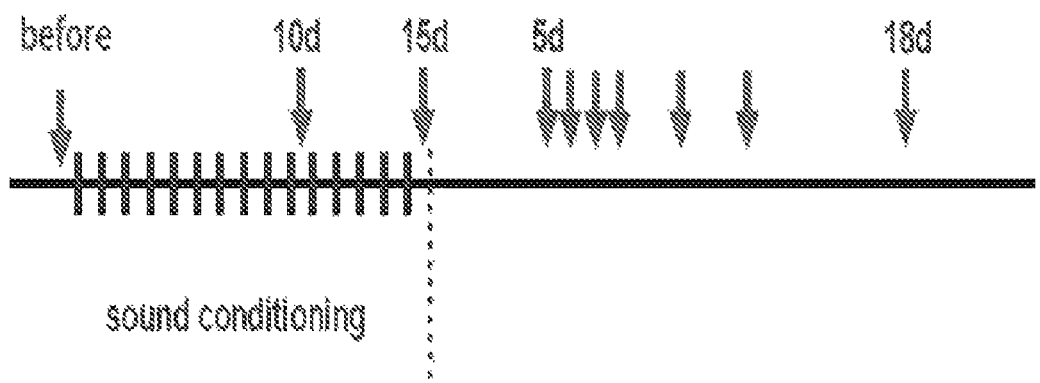
FIG. 13 is a view illustrating schedule for verifying whether or not the hearing ability improvement is continuously maintained after the acoustic signal stimulation to the right ear is stopped.

FIG. 13 is a view illustrating schedule for verifying whether the hearing ability improvement is continuously maintained after the acoustic signal stimulation to the right ear is stopped.

The hearing ability is measured from five days to eighteen days after the acoustic signal stimulation is stopped.

Figure 14:
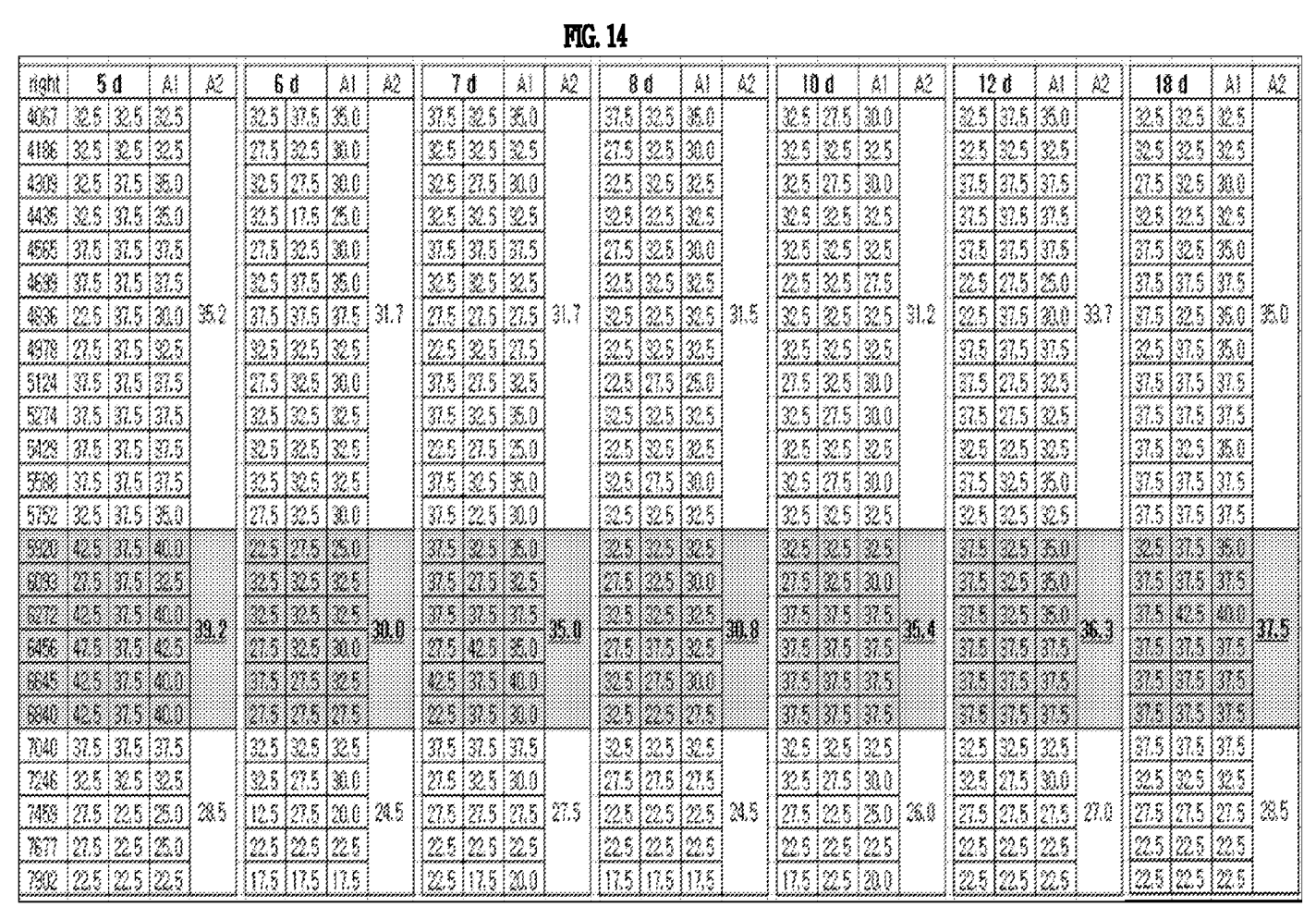
Figure 15:
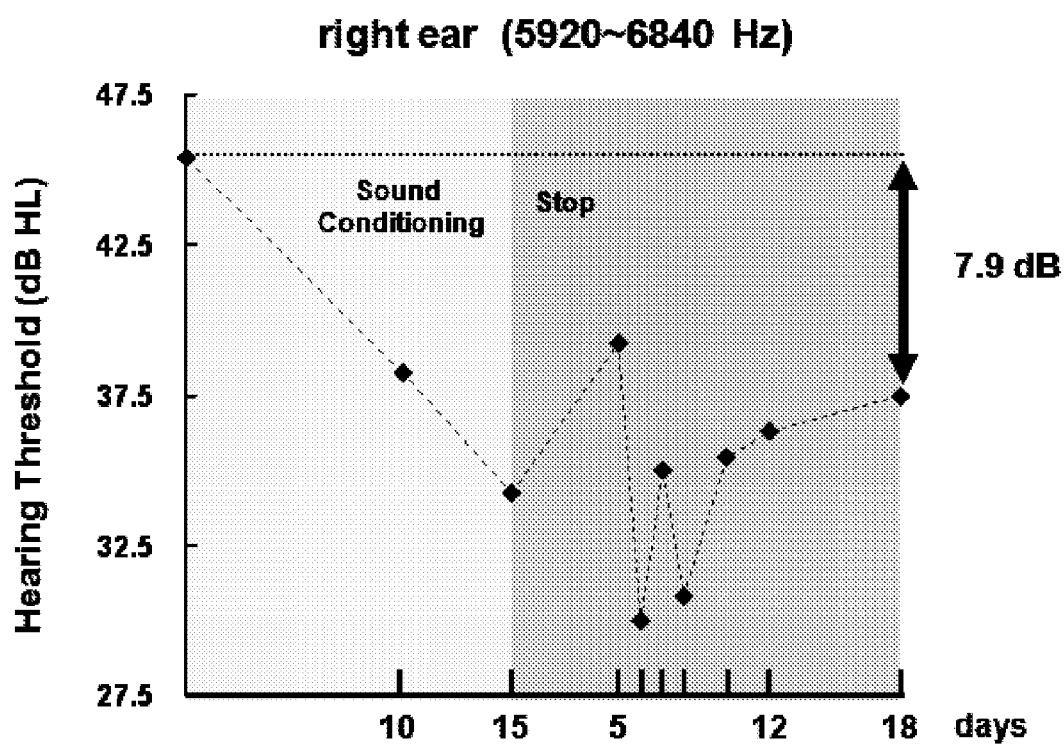
FIG. 15 is a view illustrating a graph corresponding to the table in FIG. 14.

FIG. 14 is a view illustrating a table showing hearing threshold of the right ear after the acoustic signal stimulation is stopped. FIG. 15 is a view illustrating a graph corresponding to the table in FIG. 14.

Referring to FIG. 14 and FIG. 15, the hearing ability improvement effect is maintained after the acoustic signal stimulation is stopped. Additionally, it is verified that the hearing ability is still improved by approximately 7.9 dB eighteen days after the acoustic signal stimulation is stopped.

Any reference in this specification to "one embodiment," "an embodiment," "a preferred embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to affect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method for cochlear hair cell stimulation using acoustic stimulation, the method comprising:
   (a) determining with a hearing diagnosis section of a hair cell stimulation apparatus, a frequency band corresponding to a damaged hair cell region by outputting a cochlear model interface that includes hair cell region images divided with 1/k octave resolution, wherein the k is a positive integer of above 2, and when a user selects at least one of the hair cell region images, outputting a diagnostic acoustic signal with a frequency band corresponding to the selected hair cell region image and determining a hearing threshold using a user's response information from the output diagnostic acoustic signal;
   (b) determining with a stimulation region detecting section of the hair cell stimulation apparatus, a target frequency band corresponding to the damaged hair cell region; and
   (c) outputting with a stimulation treatment section of the hair cell stimulation apparatus, a stimulating acoustic signal to the target frequency band at a preset intensity to stimulate the damaged hair cell region, wherein the preset intensity is determined by the hearing threshold of the damaged hair cell region,
   wherein the stimulating acoustic signal is at least one of amplitude modulated tone, frequency modulated tone, pulse tone, continuous tone, and amplitude modulated narrowband noise, or combination of the tones and the noise.

2. The method of claim 1, wherein in case that the damaged hair cell region is plural, a frequency band range corresponding to hair cell regions located continuously among the damaged hair cell regions is determined as the target frequency band in the step (b).

3. The method of claim 1, wherein in case that the target frequency band is plural, acoustic signals corresponding to the target frequency bands are outputted in order of damage severity or randomly in the step (c).

4. The method of claim 1, wherein in case that the target frequency band is plural, acoustic signals corresponding to the target frequency bands are outputted simultaneously in the step (c).

5. The method of claim 1, wherein the k is a positive integer of 3 to 24.

6. The method of claim 1, wherein a frequency band of a hair cell region of which hearing threshold is higher than a preset reference value is determined as the target frequency band in the step (b),
   and wherein the method further comprises:
   (d) outputting an hair cell region image corresponding to the determined target frequency band, wherein the outputted hair cell region image is visualized.

7. The method of claim 6, wherein in the step (c), the acoustic signal is outputted with an intensity higher approximately by 3 dB to 20 dB than the hearing threshold.

8. The method of claim 1, further comprising:
   in case that the type of the acoustic signal is an amplitude modulated tone, outputting a hair cell region image corresponding to the frequency band of the amplitude modulated tone, wherein amplitude variation of the amplitude modulated tone is visualized on the hair cell region image.

9. The method of claim 1, further comprising:
   in case that the type of the acoustic signal is a frequency modulated tone, outputting a hair cell region image corresponding to the frequency band of the frequency modulated tone, wherein frequency variation of the frequency modulated tone is visualized on the hair cell region image.

10. The method of claim 9, wherein the frequency modulated tone has a resolution less than ⅓ octave.

11. The method of claim 1, further comprising:
in case that the type of the acoustic signal is a continuous tone or a pulse tone, outputting a hair cell region image corresponding to the frequency band of the continuous or pulse tone acoustic signal, wherein it is sensed through the hair cell region image that the acoustic signal corresponds to at least one of the continuous tone and the pulse tone.

12. The method of claim 1, wherein the hair cell region image is outputted with different color or size depending on the extent of hearing ability improvement.

13. A recording media readable by a computer performing the method of claim 1.

14. A method for cochlear hair cell stimulation, the method comprising:
outputting with a hair cell stimulation apparatus, a cochlear model interface including hair cell region images divided with 1/k octave resolution, wherein the k is a positive integer of above 2;
outputting with the hair cell stimulation apparatus, an acoustic signal of a frequency band corresponding to at least one region selected from the above hair cell region images; and
detecting with the hair cell stimulation apparatus, a damaged hair cell region on the basis of the user's response to the outputted acoustic signal.

15. A method for providing a cochlear hair cell stimulation service stored on a non-transient machine readable medium of a server connected electrically to a client through a network, the method comprising:

(a) transmitting an application for hearing diagnosis to the client with a hair cell stimulation apparatus, wherein the application outputs a cochlear model interface including hair cell region images divided with 1/k octave resolution wherein the k is a positive integer of above 2, and when a user selects at least one of the hair cell region images, outputting a diganostic acoustic signal with a frequency band corresponding to the selected hair cell region image and determining a hearing threshold from a user's response information of the outputted diagnostic acoustic signal;

(b) receiving with the hair cell stimulation apparatus, the response information from a user in accordance with the diagnostic acoustic signal of a frequency band corresponding to at least one region selected from the above hair cell region images;

(c) determining with the hair cell stimulation apparatus, a target frequency band corresponding to damaged hair cell region on the basis of the user's response information; and (d) transmitting with the hair cell stimulation apparatus, a stimulating acoustic signal of the target frequency band at a preset intensity, wherein the intensity of the stimulating acoustic signal is determined by the hearing threshold of the damaged hair cell region;

wherein the stimulating acoustic signal is at least one of amplitude modulated tone, frequency modulated tone, pulse tone, continuous tone, and amplitude modulated narrowband noise, or combination of the tones and the noise.

* * * * *